(12) United States Patent
Puertas et al.

(10) Patent No.: US 8,017,346 B2
(45) Date of Patent: Sep. 13, 2011

(54) METHOD OF QUANTIFYING THE G PROTEIN-COUPLED RECEPTOR (GPCR)/G PROTEIN COUPLING USING A CELL MEMBRANE ARRAY

(75) Inventors: Rafael Rodriguez Puertas, Leioa-Vizcaya (ES); Gabriel Barreda Gomez, Leioa-Vizcaya (ES); Maria Teresa Giralt Rue, Leioa-Vizcaya (ES); Begona Fernandez Pastor, Castelldefels-Barcelona (ES)

(73) Assignee: Universidad Del Pais Vasco, Leioa-Vizcaya (ES)

( * ) Notice: Subject to any disclaimer, the term of this patent is extended or adjusted under 35 U.S.C. 154(b) by 577 days.

(21) Appl. No.: 11/996,965

(22) PCT Filed: Jul. 28, 2006

(86) PCT No.: PCT/ES2006/000445
§ 371 (c)(1),
(2), (4) Date: Jul. 2, 2008

(87) PCT Pub. No.: WO2007/012688
PCT Pub. Date: Feb. 1, 2007

(65) Prior Publication Data
US 2008/0318799 A1 Dec. 25, 2008

(30) Foreign Application Priority Data
Jul. 28, 2005 (ES) .................................. 200501859

(51) Int. Cl.
*G01N 33/53* (2006.01)
*C12Q 1/125* (2006.01)
(52) U.S. Cl. ............................................ 435/7.1; 435/4
(58) Field of Classification Search .................. None
See application file for complete search history.

(56) References Cited

U.S. PATENT DOCUMENTS

| | | | |
|---|---|---|---|
| 7,473,533 B2 * | 1/2009 | Carre et al. | 435/7.2 |
| 7,678,539 B2 * | 3/2010 | Fang et al. | 435/4 |
| 2003/0138853 A1 | 7/2003 | Lahiri et al. | |

FOREIGN PATENT DOCUMENTS

| | | |
|---|---|---|
| EP | 2 048 534 A1 | 4/2009 |
| WO | 03014731 A2 | 2/2003 |

OTHER PUBLICATIONS

Watson et al. Development of Flash-plate™ technology to measure [35S]GTPgammaS binding to Chinese Hamster ovary cell membranes expressing the cloned human 5-HT1B receptor. J. Biomol. Screen 3:101-105, 1998.*

Dallas-Yang et al., Detection of glucagon-dependent GTPgammaS binding in high-throughput format. Analytical Biochemistry 301:156-159, 2002.*

Ferrer, M. et al, "A Fully Automated 35SGTPyS Scintillation Proximity Assay for the High-Throughput Screening of Gi-linked G Protein Coupled Receptors", "Assay and Drug Development Technologies", 2003, pp. 261-273, vol. 1, No. 2.

Gomez, B. et al. , "Effects of central galanin administration on muscarinic cholinergic and galanin receptor G protein coupling", "Neuropeptides", Feb. 1, 2005, pp. 157-160, vol. 39.

Takeda, S. et al., "Identification of surrogate ligands for orphan G protein-coupled receptors", "Life Sciences", 2003, pp. 397-377, vol. 74.

Breivogel, Christopher S., et al., "Evidence for a new G protein-coupled cannabinoid receptor in mouse brain", "Mol. Pharmacol.", Jul. 2001, pp. 155-163, vol. 60, No. 1.

\* cited by examiner

*Primary Examiner* — Ruixiang Li
(74) *Attorney, Agent, or Firm* — Steven J. Hultquist; Kelly K. Reynolds; Hultquist IP

(57) ABSTRACT

The invention relates to a method for quantifying G protein-coupled receptor (GPCR)-G protein binding by means of using a cell membrane array, which comprises (i) putting an unlabeled candidate compound in contact with a cell membrane array in the presence of labeled GTP or of a labeled, non-hydrolyzable analog thereof, in conditions allowing the interaction between said compound and said GPCR present in said cell membranes, and between said labeled GTP or analog thereof and said G protein present in said membranes; (ii) washing; and (iii) quantifying the signal obtained due to the binding of the labeled GTP (or analog) to said G protein. It is applicable in the analysis of the interaction between compounds and cell membrane receptor proteins and of the intracellular signaling mechanisms triggering this interaction mechanism mediated by said compounds.

23 Claims, 4 Drawing Sheets

1. Striatum
2. Thalamus
3. Olfactory tract
4. Spinal ganglia
5. Cervical marrow
6. Olfactory bulb
7. Hippocampus
8. Cerebellum
9. Brain stem
10. Adipose tissue
11. Hypothalamus
12. Colliculus
13. Adipose tissue
14. Kidney
15. Adrenal glands
16. Vas deferens
17. Testicle
18. Lung
19. Spleen
20. Heart
21. Stomach
22. Small intestine
23. Liver
24. Pituitary gland

METHOD OF QUANTIFYING THE G PROTEIN-COUPLED RECEPTOR (GPCR)/G PROTEIN COUPLING USING A CELL MEMBRANE ARRAY

CROSS-REFERENCE TO RELATED APPLICATIONS

This application is a United States national phase application filed Jan. 26, 2008 under the provisions of 35 USC §371 based on International Application No. PCT/ES06/00445 filed Jul. 28, 2006, which in turn claims priority of Spanish Patent Application No. P200501859 filed Jul. 28, 2005. The disclosures of such international application and Spanish priority application are hereby incorporated herein by reference in their respective entireties, for all purposes.

FIELD OF THE INVENTION

The invention generally relates to the use of a cell membrane array containing G protein-coupled membrane receptors (GPCRs) for analyzing the interaction between compounds and cell membrane receptor proteins, as well as for analyzing the intracellular signaling mechanisms triggered by this interaction mechanism mediated by such compounds (ligands).

BACKGROUND OF THE INVENTION

G protein-coupled receptors (GPCRs) are involved in a number of physiological signaling processes at both an intracellular and intercellular level. GPCRs are hormone, neurotransmitter and neuromodulator receptors and mediate their intracellular actions through pathways in which G proteins are involved (rev: Kristiansen "Molecular mechanisms of ligand binding, signaling and regulation within the superfamily of G-protein coupled receptors: molecular modeling and mutagenesis approaches to receptor structure and function" Pharmacology and Therapeutics, 2004, 103, 21-80). G proteins intracellularly transmit the signal to effector proteins, such as enzymes and ion channels, causing changes in signaling molecules such as cAMP, cGMP, inositol phosphates, diacylglycerol, arachidonic acid and ions. Their activation and regulation is the one of the initial processes of adaptation mechanisms at cell level triggering the activation of second intracellular messengers and the activation of several signaling cascades, phosphorylating enzymes and promoting the regulation at gene level, which will ultimately give rise to a certain physiological effect.

There are two main types of G proteins, heterotrimeric G proteins, binding to GPCRs and participating in intracellular signal transduction mechanisms, and small cytoplasmic G proteins. The former are formed by three subunits, α, β and γ. The βγ subunits are closely associated and can be considered as a single functional unit. With the binding of the agonist, the receptor is activated and undergoes a conformational change resulting in an increase of its affinity for the G protein. This allows a fast GDP dissociation from its binding site in the α subunit. In normal physiological conditions, GDP is immediately replaced by GTP, the concentration of which exceeds that of GDP by several times. The change of guanine nucleotides causes a reduction in the affinity of the α subunit for the βγ complex and the subsequent dissociation of the heterotrimer, in the α subunit on one hand and the βγ dimer on the other hand. Each of the already dissociated subunits can promote the regulation of different second messengers such as 5'-3' adenosine monophosphate (cAMP) or inositol triphosphate (IP3), and activate different signaling cascades, which results in a great variety of cell functions. The active state lasts until GTP is hydrolyzed to GDP by the intrinsic GTPase activity of the Gα subunits. Once GTP has been hydrolyzed to GDP, the α-GDP and βγ subunits bind again and become inactive.

All the heterotrimeric G proteins follow the same activation/deactivation cycle, thus reversibly allowing a specific intracellular signal transmission. When a GDP molecule binds to the α subunit, the complex is associated with the βγ subunits, thus forming an inactive heterotrimer. Despite the fact that GDP bound to the α subunit can bind to the receptor without βγ, the association with the receptor is highly increased in the presence of βγ.

However, not all the receptors activating G proteins are members of the GPCR superfamily. The activation of G proteins is further involved in the transduction signal mediated by several tyrosine-kinase receptors, such as the epidermal growth factor (EGF) receptor, insulin and growth factors and insulin-like growth factors I and II.

GPCRs are involved in pathologies such as pain, cancer, asthma, inflammation, metabolic, immune, gastrointestinal and neurological disorders. About 500 different GPCRs are known and all of them share the typical molecular structure of 7 hydrophobic domains with about 30 amino acid each traversing the cell membrane, with an extracellular carboxy end and an intracellular amino. The GPCR superfamily comprises receptor for several hormones, neurotransmitters, paracrines and neuromodulators with very important physiological functions. The alteration in the operation of these receptors causes human diseases, and many of these GPCRs are targets for many drugs and abuse drugs. This superfamily includes receptors for several types of endogenous ligands such as amines, peptides, amino acids, glycoproteins, phospholipids, nucleotides, calcium ions, etc. It has been estimated that approximately 80% of known hormones and neurotransmitters activate signal translation mechanisms by means of activating GPCRs, which represent approximately 30-45% of the targets for drugs. GPCRs therefore constitute excellent therapeutic targets for modulating ligand:receptor interactions, which is primarily interesting for developing new drugs.

The development of recombinant DNA techniques has currently allowed obtaining cell preparations overexpressing a certain GPCR subtype. The preparations enriched with membrane receptors are commercially available (for example Amersham Biosciences, PerkinElmer Life and Analytical Sciences), and can be obtained as donations from other research groups or they can be prepared in a cell culture laboratory by means of transfecting cell lines.

GPCRs currently constitute the therapeutic target of more than 30% of the drugs in the market and their sales have produced a large part of the profits of pharmaceutical companies, for example in 2002, the 30 most sold drugs worldwide generated more than 35 billion dollars (Glasel "Emerging Concepts in GPCR research and their implications for drug discovery" Decision Resources 2004).

BRIEF DESCRIPTION OF THE DRAWINGS

FIG. 3A shows the baseline [$^{35}$S] GTPγS fixing, in the absence of drugs, due to the constitutive GPCR activity. FIG. 3B shows the stimulation of [$^{35}$S] GTPγS fixing by the agonist drug of the cannabinoid receptor CB1, WIN 55212-2. The greater intensity of gray indicates a greater radioligand fixing in the microwells incubated in the presence of agonist drug.

DETAILED DESCRIPTION OF THE INVENTION

Figure 1:
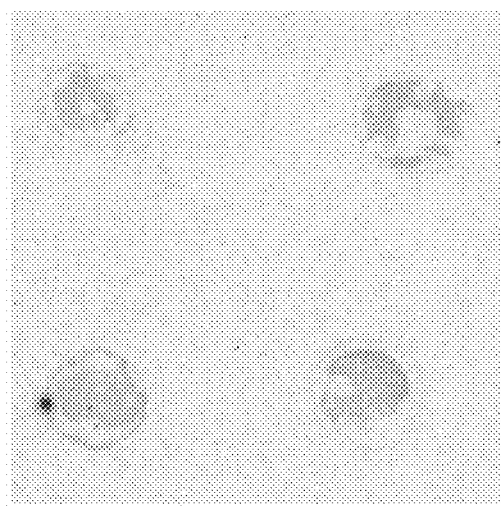
FIG. 1 shows an autoradiographic image showing the labeling obtained from a membrane homogenate deposited on a gelatinized support. The diameter of each circle is 1.5 mm.

The present invention generally relates to a cell membrane array. The invention is specifically based on a cell membrane array containing G protein-coupled membrane receptors (GPCRs) for analyzing the interaction of compounds (for example drugs, etc.) and cell membrane receptor proteins, as well as for analyzing the intracellular signaling mechanisms triggered by this interaction mechanism mediated by such compounds (ligands).

In an aspect, the invention relates to a method for quantifying G protein-coupled receptor (GPCR)-G protein binding by means of using a cell membrane array comprising:
(i) putting an unlabeled candidate compound in contact with a cell membrane array in the presence of labeled GTP or of a labeled, non-hydrolyzable analog thereof, in conditions allowing the interaction between said compound and said GPCR present in said cell membranes, and between said labeled GTP or analog thereof and said G protein also present in said cell membranes;
(ii) washing said membrane array to eliminate said labeled GTP or labeled, non-hydrolyzable analog thereof that is not bound to said G protein; and
(iii) quantifying the signal obtained due to the binding of said labeled GTP or labeled, non-hydrolyzable analog thereof to said G protein.

The term "cell membranes" relates to a cell membrane homogenate containing the protein receptor-transduction protein complexes in a functional state.

The cell membranes of the present invention can come from vesicles, liposomes, lipid monolayer membranes, parts of membranes or complete cell membranes, etc. Lipid bilayer membranes will preferably incorporate ionophores, ion channels or analytes, such as antibodies, enzymes, lectins, chelating agents, etc.

Cell membrane homogenates can be obtained by homogenization and centrifugation processes known in the state of the art starting from any tissue, organ or cell type of any member of an animal species, including human species, by way of illustration, it can be a mammal, such as a primate, a domestic animal, a rodent, pathology animal models, transgenic animals, a normal human being or a human being with any type of pathology or pharmacological treatment, etc.

Tissue homogenization methods are well known in the state of the art. By way of illustration, the protocols described in the example included herein were followed to homogenize the cell membranes of the array of the invention.

A support on which multiple cell membrane homogenate microdeposits were fixed was used to generate the membrane array of the present invention. The term "microdeposits" relates to membrane deposits which will contain membrane amounts of less than micrograms. The shape of the microdeposits of the array will be of the type that is most suitable for the needs of the invention, they will preferably be circular, oval or with any similar shape resulting from the particular method used to produce the array. The density of all the microdeposits of the array is at least, 1/cm$^2$ and normally at least 10/cm$^2$, without exceeding 1,000/cm$^2$. The size of the support will be standard such that it allows using commercial microspotters and scanners developed for DNA arrays for example. Each support is further provided with an identification system which allows identifying each protein array and allows automating the system, such as a bar code for example.

The size and shape of the support will be standardized, such that it facilitates automating the system. The shape of the support can be rectangular or circular. The support will preferably have a rectangular shape, with a size of approximately 10 mm to 200 mm, normally with a length of 40 mm to 150 mm and a width of approximately 10 mm to 200 mm, preferably 20 mm to 120 mm, and with a thickness of approximately 0.01 mm to 5 mm, normally 0.1 mm to 2 mm. As a non-limiting illustrative example, the size of the support will be similar to that of a slide, i.e., 25 mm wide, 75 mm long and 1 mm thick.

The microdeposits will be arranged in the array according to a pattern along the length and width of the surface of the support, such as for example in rows and columns forming a grid and similar patterns.

The composition of the supports will be of glass or plastic material, such as plastic polymers, organic polymers, etc., such that it allows a smooth surface, or substantially planar surface or a surface with irregularities, such as depressions or elevations. The surface can also be porous and preferably transparent when it must be scanned for quantification. The composition of the support includes, for example, noble or seminoble metals, such as gold or silver, glass, metal or non-metal oxides, silicone, ammonium phosphate, polymers and plastics such as polyvinylchloride, polyvinylalcohol, etc.

The array of the present invention can optionally be coated with any type of material or substance which will normally increase the affinity of the cell membrane microdeposits to the support. The membranes will be fixed to the support by means of using inert substances promoting the immobilization of the membranes in said supports, and which in turn allow keeping the membrane preparations in a functional state, i.e. with the membrane proteins conserving the suitable spatial conformation to allow their function, the fixing of drugs to receptor proteins and the coupling of these receptors to the intracellular signal transduction mechanisms under conditions of contact and washing, i.e. the microdeposits must maintain their position and functionality when the air-water interface is changed during the processing of the method of the invention.

Polylysine, gelatin, orthophosphoric acid, lignin, agar-agar, etc. are non-limiting, illustrative examples of said inert substances.

The term "G protein-coupled receptor (GPCR)" relates to cell membrane receptors with seven transmembrane domains and which are associated to their coeffector, the G protein. These receptors transduce the extracellular signal (compound/ligand binding) into an intracellular signal (G protein activation). The GPCR protein superfamily is the largest known protein family, the members of which participate in virtually all intracellular biological processes and bind virtually all types of biological macromolecules as ligands.

In a normal situation, as occurs in nature, after a compound binds to the membrane GPCR, a conformational change of the GPCR occurs such that the protein binding sites of the G protein which were previously covered are exposed. This interaction catalyzes a guanine nucleotide change, resulting in the binding of a GTP to the α subunit of the G protein. This binding makes the Gα-GTP dissociate from the Gβγ subunits. As a result of the intrinsic GTPase activity of the Gα subunit, the bound GTP is hydrolyzed to GDP, the system thus returning to its initial heterotrimer state.

For the purpose of eliminating any residue of drug or compound that is not bound to the microdeposits as well as of radioligand that is not specifically bound to the membrane in each microwell, the method of the invention further includes an array washing step. Conventional methods known by persons skilled in the art are used to carry out said washing, including, by way of a non-limiting illustration, buffers and solutions such as those described in the example of the present document.

GTP or a non-hydrolyzable analog thereof has been used to develop the method of the invention. The method of the invention also includes the quantification of the signal obtained due to the binding of said labeled GTP or labeled, non-hydrolyzable analog thereof to said G protein. The signal can be quantified by means of any technique described in the current state of the art of arrays and well known by persons skilled in the art, such as for example quantification techniques, by means software, used in nucleic acid arrays.

To determine the effect of GPCR-G protein binding on second cellular messengers, and thus analyze its possible action on cell signaling cascades, in another aspect, the invention is based on a method for analyzing GPCR-G protein binding and quantifying the effect promoted by this binding on a second intracellular messenger by means of using a cell membrane array comprising:
  (i) putting an unlabeled candidate compound in contact with a cell membrane array in the presence of GTP or of an analog thereof and a labeled second cellular messenger formation activity marker, in conditions allowing the interaction between said compound and said GPCR present in said cell membranes, between said GTP or analog thereof and said G protein present in said cell membranes, between the active G protein and an effector molecule also present in said cell membranes, and between said effector molecule and said labeled second cellular messenger formation activity marker;
  (ii) washing said membrane array to eliminate said labeled second cellular messenger formation activity marker that is not bound to said effector molecule; and
  (iii) quantifying the signal obtained due to the binding of said labeled second cellular messenger formation activity marker to said effector molecule, where the intensity of the signal obtained is proportional to the effect promoted by the GPCR-G protein binding on said second intracellular messenger.

The term "second cellular messenger formation activity marker" as used in the present invention, relates to a molecule having the capacity to bind to an effector molecule included in the cell membranes of the invention and the binding of which indicates the formation of a second cellular messenger. The term "effector molecule" relates to a molecule included in the cell membranes of the invention and which its ligand, the second cellular messenger formation activity marker, can bind to, which marker is added to the array in the method of the invention and, is also labeled.

In a particular embodiment, the previously described method includes the fact that said GTP or hydrolyzable or non-hydrolyzable analog thereof is labeled. In this case, the labeling will be different from that used for the second cellular messenger formation activity marker, i.e., the labeling will be such that it allows distinguishing both signals. This methodology, allows for example, using fluorescent markers emitting a different wavelength and which can therefore be distinguished by their signal for GTP or hydrolyzable or non-hydrolyzable analog thereof and the second cellular messenger formation activity marker.

In another particular embodiment, in the previously described method the labeled second cellular messenger formation activity marker is labeled ATP or an analog thereof. In a still more particular embodiment, the labeled second cellular messenger formation activity marker is a labeled non-hydrolyzable analog of phosphatidylinositol 4,5 diphosphate (PtdIns (4,5) P2) or an analog thereof.

In another aspect, the present invention is based on a method for quantifying compound-GPCR binding by means of using a cell membrane array comprising:
  (i) putting a labeled candidate compound in contact with a cell membrane array in the presence or absence of GTP or of an analog thereof in conditions allowing the interaction between said compound and said GPCR present in said cell membranes;
  (ii) washing said membrane array to eliminate the labeled compound that is not bound to said GPCR; and
  (iii) quantifying/analyzing the signal obtained due to the binding of said labeled compound to said GPCR, where the intensity of the signal obtained is proportional to the degree of candidate compound-GPCR interaction.

As described previously, the binding of a GTP to the α subunit of the G protein makes the Gα-GTP complex dissociate from the Gβγ subunits. The bound GTP hydrolyzes to GDP, the system thus returning to its initial heterotrimer state. In the methods of the present invention, a GTP or non-hydrolyzable analog thereof is used. In a particular embodiment, in any of the methods described in the present invention, the non-hydrolyzable GTP analog used is GTPγS. This GTPγS will be labeled such that it can be detected and quantified in the array samples. There are different GTPγS labeling methods and techniques described in the state of the art.

In a particular embodiment, said GTPγS is radioactively or fluorescently labeled. In a more particular embodiment, said GTPγS is [$^{35}$S]GTPγS, 2'(3')-O—(N-methyl-3'-anthraniloyl)-GTPγS or BODIPY-FL-GTPγS.

The signal can be quantified by means of any technique described in the current state of the art of arrays and well known by persons skilled in the art, such as for example, quantification techniques, by means of software, used in nucleic acid arrays.

Reception quantification techniques, both in isolated cell membranes (fixing of radioligands to membranes) and in tissue sections (receptor autoradiography), allow characterizing pharmacological parameters such as receptor density (Bmax) and affinity constants (Kd) of the different specific radioligands of a certain receptor protein.

The quantification technique of the fixing of guanosine 5'-O-3'-thiotriphosphate (GTPγS) to the α subunit of the G protein, with radioligands which can be detected by radiometric methods such as [$^{35}$S]GTPγS, allows quantifying the functional receptor-G protein coupling promoted by drugs both in tissue sections and in tissue and cell membrane homogenates overexpressing a certain GPCR (Payne et al. "Mechanisms of ligand binding and efficacy at the human D2 (short) dopamine receptor". J. Neurochem., 2002, 82, 1106-1117; Roberts et al., Mechanisms of agonist action at D2 dopamine receptors. Mol Pharmacol., 2004, 66, 1573-1579). This method also allows using fluorescent markers such as 2'(3')-O—(N-methyl-3'-anthraniloyl)-GTPγS (mant-GTPγS). This method allows analyzing effective concentration 50 (EC50) values when the receptor is activated by a specific agonist (Seifert et al., "Functional differences between full and partial agonists: evidence for ligand-specific receptor conformations". J Pharmacol Exp Ther., 2001, 297, 1218-1226). The drugs acting as antagonists will no activate G protein. A novel type of drugs can even be identified, which drugs promote the uncoupling of the G protein receptor in the baseline state, in absence of activation, decreasing the constitutive GTP fixing to G protein; they are the compounds known as inverse agonists (Newman-Tancredi et al., "Differential modulation by GTPgammaS of agonist and inverse agonist binding to h5-HT (1A) receptors revealed by [3H]-WAY100,635". Br J. Pharmacol., 2001, 132, 518-524). This latter type of drugs forms a new and promising therapeutic progress which is very interesting for the pharmacological industry for the treatment of those diseases occurring as a result of a baseline or anomalous constitutive activity of the organism.

In an aspect, in the methods described in the present invention, each of the microdeposits of said array is formed by isolated cell membranes from cell lines overexpressing a certain G protein-coupled receptor subtype or any genetic variation thereof.

The term "receptor subtype" relates to each of the different G protein-coupled protein molecules receiving and transmitting signals whereby the intracellular transmission of live organisms is regulated. Each receptor subtype is pharmacologically identified according to its different affinity and selectivity for both endogenous ligands and drugs.

According to this aspect of the invention, the proteins included in one of the microdeposits will be different from those included in another microdeposit of the same array. In this sense, one and the same array will include a plurality of different proteins included in different microdeposits. An array normally contains at least two GPCR subtypes. The array preferably contains 10 different subtypes, and more preferably the array contains at least 50 different subtypes. Still more preferably, the array contains at least 100 different subtypes. The array can alternatively contain at least 1,000 different subtype receptors or more than $10^4$.

In a particular embodiment, the G protein-coupled receptor subtype is a muscarinic acetylcholine receptor such as $M_1$, $M_2$, $M_3$, $M_4$, $M_5$; a dopamine receptor such as $D_1$, $D_2$, $D_3$, $D_4$, $D_5$; an adrenergic receptor such as $\alpha_{1A}$, $\alpha_{1B}$, $\alpha_{1D}$, $\alpha_{2A}$, $\alpha_{2B}$, $\alpha_{2C}$, $\beta_1$, $\beta_2$, $\beta_3$ $\beta_4$; or any of the GPCR subtypes for serotonin, etc.

In another aspect, in the methods described in the present invention, each of the microdeposits of said array is formed by isolated cell membranes from cell lines overexpressing a certain G protein subtype or any genetic variation thereof.

"G protein subtype" is defined by the each of the different protein molecules fixing guanine nucleotides and the activation of which through GPCRs causes a response in an effector system such as the or phospholipase C enzymes. Based on their biological function and on the homology of their amino acid sequences, Gα proteins can be classified into three large families ($G_s$, $G_{i/o}$, $G_q$). There are also five Gβ and seven Gγ described in the literature, which increase the possible number of different G protein subtypes.

In a particular embodiment, and according to the α subunits of the G protein, the G protein subtypes are each of the possible subtypes of three families $G_s$, $G_{i/o}$, $G_q$.

In a particular embodiment, the candidate compound used in the methods described in the present invention is a chemical compound or a biological product obtained by chemical synthesis and/or isolated from a known or unknown (live or dead) organism. Examples of candidate compounds include drugs, molecules with affinity and selectivity for different GPCR subtypes, for example, antibodies or fragments thereof. The term "antibody" includes monoclonal, polyclonal, recombinant, chimeric antibodies and fragments thereof.

Each of the microdeposits of the array can further be formed by one and the same protein but in different amounts.

The selection of a potential drug or compound for a certain GPCR of a certain organ, tissue or even cell is an extremely important factor and must therefore be considered and monitored in the drug selection process. Many GPCRs and mutants thereof are related to the development of certain tumors, and some GPCRs are distributed in a certain type of tissue, for example, opioid receptors and biogenic amine receptors are mostly found in the central nervous system. In the same way, some of these GPCRs are associated with certain known physiological and pharmacological functions. For example, some chemokine GPCRs act as cofactors in HIV infection. The arrays of the present invention can be used to manufacture specific arrays for a certain tissue-specific topic of interest, with specific functions in physiology and pharmacology.

The membrane homogenates obtained from normal and pathological tissue can be used to prepare a membrane of the present invention such that it can be used to compare the pharmacological and physiological characteristics of said tissue. For this reason, in a particular embodiment, in the methods of the present invention, each of the microdeposits is formed by isolated membranes from different tissue of one and the same subject, or one and the same tissue of different individuals, of one and the one and the same species, of different species or of genetically modified species. In a more particular embodiment, said tissue from one and the one and the same subject comes from one and the same organ or from different organs. In an even more particular embodiment, each of the microdeposits is formed by isolated membranes from cell lines or tissue obtained from individuals with different pathologies and/or pharmacological treatments.

Example 1

Basic Design for a Cell Membrane Array with Cell Membranes Isolated from Rat Brain for Analyzing the Coupling of Cannabinoid Receptors to G Proteins I. Materials and Methods
Materials The [$^{35}$S] GTPγS (1,250 Ci/mmol) radioligand was obtained from DuPont NEN (Brussels, Belgium). DL-dithiothreitol (DTT), guanosine-5'-diphosphate (GDP), GTPγS, tricine and WIN 55212-2 were obtained from Sigma (St. Louis, USA). The [$^{14}$C]-microscales were provided by Amersham Biosciences (Barcelona, Spain). The Kodak Biomax MR β-sensitive film was provided by Amersham Biosciences. The remaining reagents were obtained from different companies with a suitable degree of purity for neurochemical studies.
Methods Male Sprague-Dawley rats with a weight comprised between 250 and 275 g from the animal housing unit of the University of the Basque Country were used to conduct this study. After the animals were anesthetized with chloral hydrate at a dose of 400 mg/kg, they were sacrificed and the brain was then dissected. These samples were stored at −70° C. until they were processed.

Membranes from rat cerebral cortex were used to conduct this experiment. Specifically, approximately 1 g of tissue was thawed ad homogenized in 30 volumes of homogenization buffer (50 mM Tris-HCl, 3 mM $MgCl_2$, 1 mM EGTA, pH 7.4) supplemented with 0.25 M sucrose at 4° C. The tissue homogenate was then centrifuged at 1,000×g for 5 minutes at 4° C. and the supernatant was centrifuged again at 40,000×g for 10 minutes at 4° C. The supernatant was discarded and the pellets were resuspended in homogenization buffer, after which they were again centrifuged at 40,000×g for 10 minutes at 4° C.

The pellets were resuspended in 10 volumes of homogenization buffer, 1 ml aliquots were carried out and centrifuged for 15 minutes at 14,000 rpm. The tubes were finally decanted and the pellets were frozen at −70° C., except for one aliquot which was used to determine the protein concentration. To that end, the Bradford method, consisting of determining the protein concentration from the absorbance by means of a standard curve with known and increasing bovine serum albumin concentrations (Bradford M M., 1976 A rapid and sensitive method for the quantitation of microgram quantities of protein utilizing the principle of protein-dye binding. Anal Biochem. May 7; 72:248-54) was used.

The cell membrane device was prepared by resuspending one of the rat cortex membrane aliquots in assay buffer with 10% polylysine. 1 μl of this homogenate was placed in each microwell of the slide. These slides were manufactured with a hydrophobic resin mask delimiting each microwell so as to prevent the dispersion of sample microdrops (manufactured by Tekniker, Eibar, Spain). These cell membrane samples with the inoculated membrane samples were allowed to dry for 20 minutes at room temperature and the assay was carried out.

The assay consisted of quantifying the coupling of receptors to G proteins. To that end, the tissue sections were incubated with the 0.04 nM [$^{35}$S] GTPγS radioligand and the specific cannabinoid agonist, WIN 55212-2 (Rodríguez-Puertas et al., 2000. Autoradiography of receptor-activated G-proteins in post mortem human brain. Neuroscience. 96(1):169-80) according to the following experimental protocol:

The cell membrane devices were pre-incubated in assay buffer at pH 7.7 (50 mM Tris-HCl, 3 mM $MgCl_2$, 0.2 mM EGTA, 100 mM NaCl, 3 mU/ml adenosine deaminase, 2 mM GDP and 1 mM DTT) for 30 minutes at room temperature to eliminate the presence of endogenous neurotransmitters which may be present in the isolated membrane preparations. The slide was then incubated for 2 hours at 30° C. in the previous assay buffer, to which the following substances were added according to the different conditions of the experiment:
  Baseline: 0.04 nM [$^{35}$S] GTPγS
  Activated by agonist: 0.04 nM [$^{35}$S] GTPγS+1 μM WIN 55212-2

Once this time had elapsed, 2 washings of 15 minutes in the buffer 50 mM Tris-HCl, pH 7.4 at 4° C. were carried out to eliminate both the drug and the [$^{35}$S] GTPγS radioligand that was not specifically bound to the membranes in each microwell. After the second washing, the sections were submersed in distilled water at 4° C. to eliminate the salts of the washing buffer and the slide was dried by means of applying a cold air current.

The cell membrane devices were then exposed to a radiosensitive film (Kodak Biomax MR) for 48 hours. After this time had elapsed, it was developed in a manner similar to a photographic film. This film was digitized by means of a transparency scanner.

The labeling was quantified in optical densities by means of a computerized image analysis system (NIH-image program). The results are expressed in stimulation percentages over the baseline state by means of the following formula: (stimulated×100/baseline)−100.

II. Results

Figure 2:
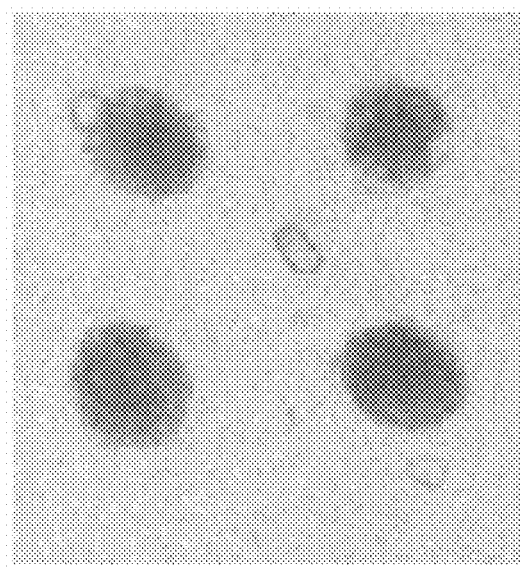
FIG. 2 shows an autoradiographic image showing the labeling obtained from a homogenate of membranes mixed with polylysine deposited on a support with hydrophobic resin to delimit each microwell. The diameter of each circle is 1.5 mm.
Figure 3:
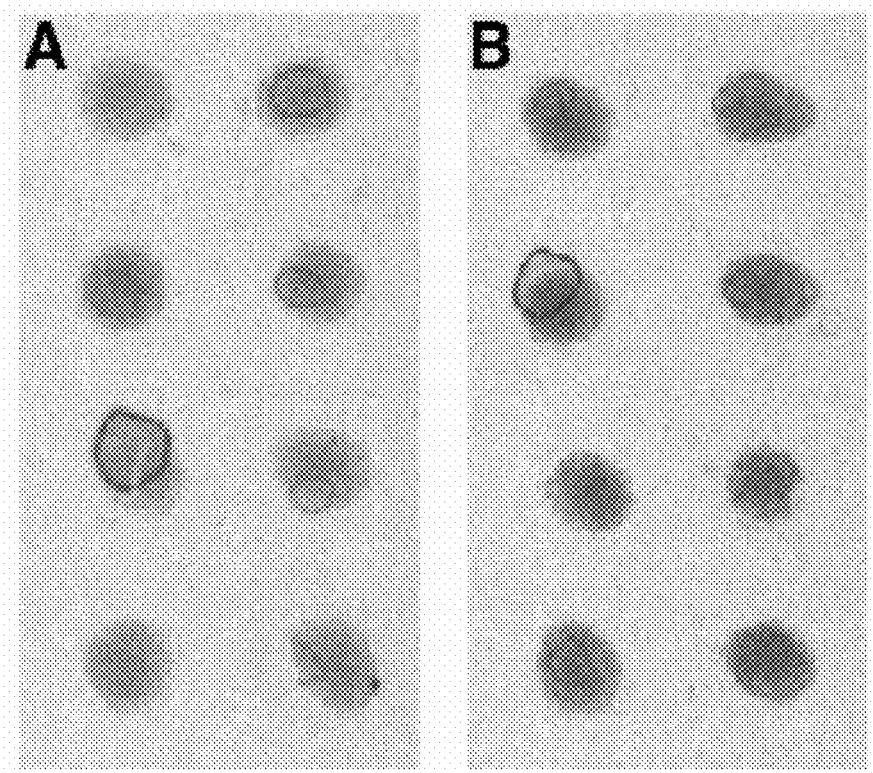
FIG. 3 shows the tests of the cell membrane array prototype generated from membrane homogenates from rat cerebral cortex tissue samples.

Heterogeneous microdeposits were obtained upon applying a membrane homogenate (without polylysine) on gelatinized slides (FIG. 1), however, when the membrane homogenate was prepared with 10% polylysine and was placed on the slides in which each microwell was previously labeled with a hydrophobic resin mask, the generated circles with the labeling were quite homogeneous (FIG. 2).

The mean values of the sum of all the microwells expressed as stimulation percentages over the baselines of the [$^{35}$S] GTPγS fixing induced by WIN 55212-2 in the cell membrane device from rat cerebral cortex were 10.2±2.7% (Table 1).

Table 1 shows the results of the [$^{35}$S] GTPγS fixing in the baseline condition (absence of drug) and in the stimulation condition with the cannabinoid agonist WIN 55212-2, obtained in the cell membrane device from rat cerebral cortex. The values are expressed in optical densities and correspond to each of the different microwells. The lower part of the table shows the mean value and the standard error for both experimental conditions.

TABLE 1

| [$^{35}$S]GTPγS fixing in absence of drug (baseline) and after stimulation with the cannabinoid agonist WIN 55212-2 | |
|---|---|
| Baseline (n = 16) | WIN 55,212(1 μM) (n = 13) |
| 7061 | 7505 |
| 8482 | 8886 |
| 7237 | 7468 |
| 8518 | 8688 |
| 8185 | 9161 |
| 8185 | 8869 |
| 8239 | 9791 |
| 8561 | 9743 |
| 7083 | 9473 |
| 8846 | 8332 |
| 8939 | 9093 |
| 8219 | 8169 |
| 7066 | 9439 |
| 7868 | |
| 8101 | |
| 7444 | |
| 8002.1 ± 172.8 | 8816.7 ± 212.4 |

III. Discussion

The present invention shows that the coupling of the GPCR receptor to the G protein is conserved in cell membrane devices from rat cerebral cortex and that the [$^{35}$S] GTPγS technique is a useful tool for evaluating this functional response in this type of preparations and devices. The fact that the functionality of the receptors is conserved at this level also indicates that other intracellular signaling pathways, such as phosphoinositide or cAMP pathways, could also be conserved and therefore this device could also be used to quantify this type of response or other responses in which membrane proteins are involved.

This same assay has also been carried out on cell membrane devices from tissue samples of different brain areas and cells (FIG. 2) on which different drugs have been assayed. In these experiments, it has been verified that the already mentioned properties of these devices are reproduced, therefore it can be concluded that cell membrane devices are a useful tool for evaluating the response of membrane receptors to a certain compound, at least at the level of the coupling to the G protein.

Example 2

Study of the Specific Activity of Different Galanin Receptor Ligands

A set of galanin receptor ligands has been studied for the purpose of determining the specific activity of each molecule.
I. Materials and Methods
Animals 5 male Sprague Dawley rats (250-275 g) were anesthetized and sacrificed according to the guide approved by the Ethics Committee of the Faculty of Medicine of the University of the Basque Country, following the internationally accepted guidelines (86/609/EEC). The organs and tissue which were to be used in the experiment (pancreas, stomach, small intestine, spleen, heart, lung, liver, testicle, vas deferens, kidney, suprarenal glands, bone marrow and brain: frontal cortex, striatum, brain stem, pituitary gland, olfactory nuclei, hippocampus, hypothalamus, thalamus, colliculus and cerebellum) were then removed. These samples were stored at −70° C. until the experiment was carried out.
Membrane Preparation The tissue samples (1 g) were homogenized using a teflon-glass homogenizer (10 strokes at 1,500 rpm) in 30 volumes of homogenization buffer [1 mM ethylene glycol-bis(β-aminoethyl)-N,N,N',N'-tetraacetic acid (EGTA), 3 mM $MgCl_2$, 1 mM dithiothreitol (DTT) and 50 mM Tris-HCl, pH 7.4] supplemented with 0.25 mM sucrose. The crude homogenate was centrifuged at 3,000×g and at 4° C. for 5 minutes and the resulting supernatant was again centrifuged at 40,000×g for 10 minutes (4° C.). The pellet was washed in 20 volumes of homogenization buffer and re-centrifuged in the same conditions. Aliquots were carried out and stored at −70° C. The protein content was determined according to the Bradford method [Bradford M M., Anal Biochem 1976; 72:248-54] using bovine serum albumin (BSA) as a standard.
Tissue Array Preparation 1 mg/ml aliquots of each tissue were taken and with this suspension, 1 µl microspots were made on glass supports (slides) which were previously treated with concentrated orthophosphoric acid (85%); to that end, the slides were first washed with acetone and then with anhydrous isopropanol, they were dried and finally submersed in concentrated orthophosphoric acid (85%) for 24 hours, they were washed with distilled water (Millipore) and air-dried. The arrays were frozen at −70° C. until the experiment was carried out.
[$^{35}$S] GTPγS Autoradiography The slides with tissue sections were allowed to dry for 15 minutes at room temperature. The tissue section were then pre-incubated in assay buffer at pH 7.4 [50 mM Tris-HCl, 3 mM MgCl2, 0.2 mM EGTA, 100 mM NaCl, 3 mU/ml adenosine deaminase] for 20 minutes at room temperature to eliminate, as much as possible, the presence of endogenous neurotransmitters; afterwards, the sections were pre-incubated again in the assay buffer supplemented with guanosine diphosphate (GDP) (2 mM) and DTT (1 mM).

The slides were then incubated for 2 hours at 30° C. in the previous assay buffer, to which the following substances were added according to the different conditions of the experiment:
Baseline: 0.04 nM [$^{35}$S] GTPγS
Activated: 0.04 nM [$^{35}$S] GTPγS+agonist
Inhibited: 0.04 nM [$^{35}$S]GTPγS+agonist+antagonist
Non-specific: 0.04 nM [$^{35}$S] GTPγS+10 µM GTPγS Once this time had elapsed, 2 washings of 15 minutes in the buffer 50 mM Tris-HCl, pH 7.4 at 4° C. were carried out. After the second washing, the sections were submersed in distilled water at 4° C. to eliminate the salts and the slide was dried by means of applying a cold air current.

The slides with the corresponding sections were then exposed to a radiosensitive film (Kodak Biomax MR) which was developed in a manner similar to a photographic film. The labeling was quantified according to the different gray densities at nCi/g of tissue equivalent. To that end, each film was exposed together with the previously calibrated commercial standards (Amersham). The quantification was carried out with microscopic anatomical resolution in a computerized image analysis system, using NIH-image software, of G protein activation.

Figure 4:
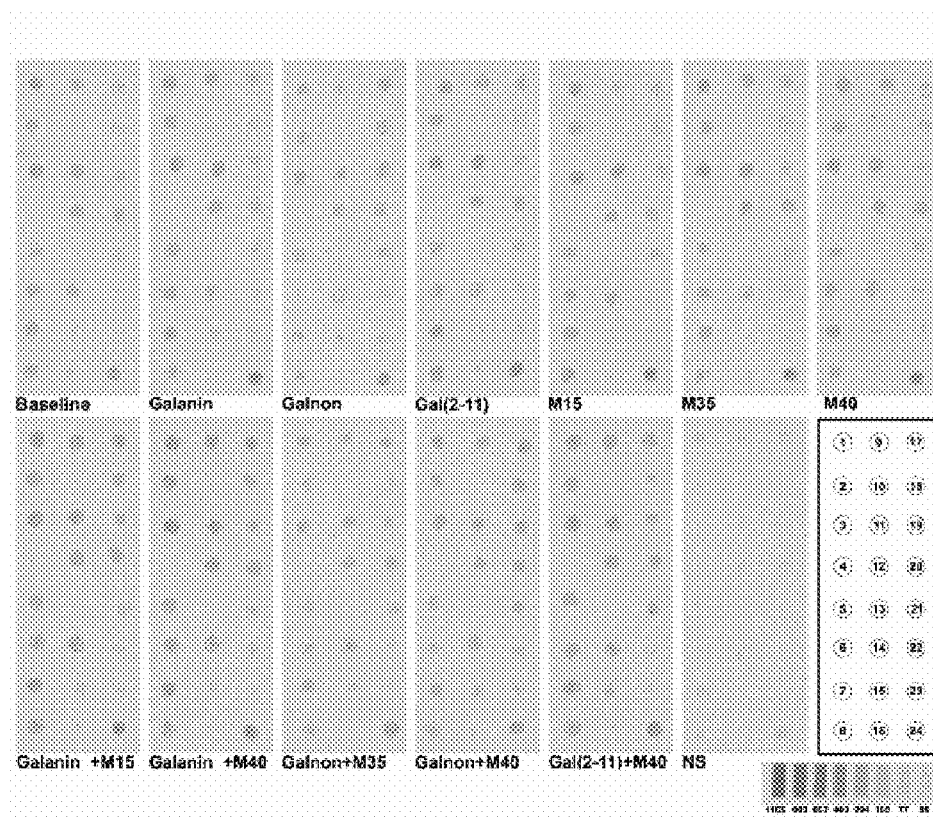
FIG. 4 shows the immobilization of isolated cell membranes and shows [$^{35}$S]GTPγS fixing in the absence (baseline) and the presence of different galanin receptors ligands [Galanin, Galnon, Gal (2-11), M15, M35, M40 and combinations thereof, such as Galanin+M15, Galanin+M40, Galnon+M35, Galnon+M40 and Gal (2-11)+M40]. The nonspecific fixing is determined in the presence of 10 μM GTPγS (NS). The $^{14}$C standard and the values in nCi/gt.e. assigned to each color are shown in the lower right-hand corner.
Figure 5:
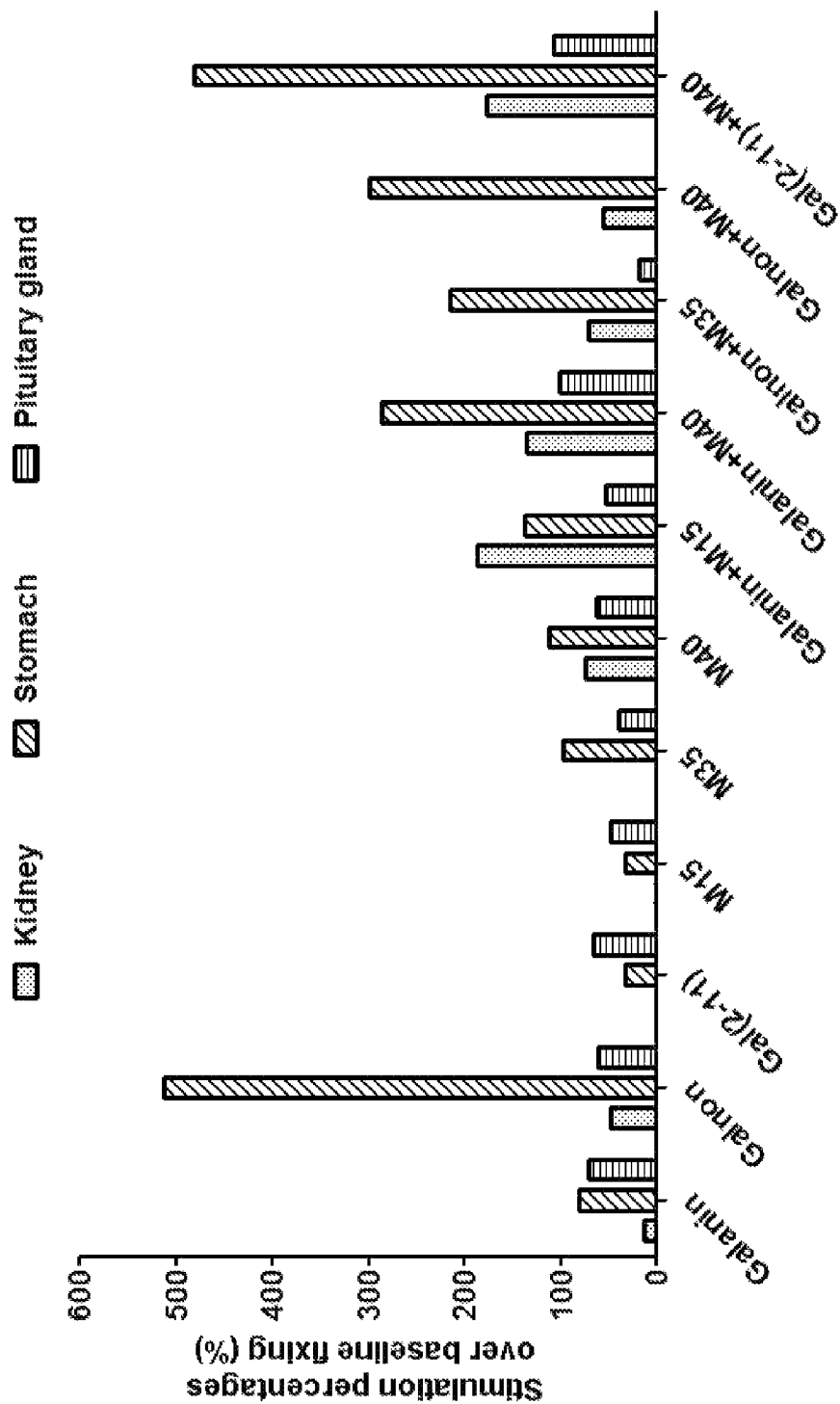
FIG. 5 is a bar graph showing the stimulation percentages over baseline [$^{35}$S]GTPγS fixing in the presence of different galanin receptor ligands [Galanin, Galnon, Gal (2-11), M15, M35, M40 and combinations thereof, such as Galanin+M15, Galanin+M40, Galnon+M35, Galnon+M40 and Gal (2-11)+M40] in the kidney, stomach and pituitary gland quantified in the tissue arrays.

The following ligands were used to study [$^{35}$S] GTPγS fixing in the absence (baseline) and in the presence of galanin receptor ligands: galanin, galnon, gal (2-11), M15 [galanin-(1-13)-substance P-5-11 amide], M35 [galanin-(1-13)-bradykinin-(2,9) amide] and M40 [galanin-(1-13)-Pro-Pro-Ala-Leu-Ala-Leu-Ala-Leu-Ala amide].
II. Results
[$^{35}$S] GTPγS Fixing in the Absence (Baseline) and in the Presence of Galanin Ligands A set of galanin receptor ligands has been studied for the purpose of determining the specific activity of each molecule (FIG. 4). Said figure shows how in some tissue (e.g., pituitary gland), there is an increase of [$^{35}$S]GTPγS fixing in the presence of galanin, galnon, gal (2-11), M15, M35 and M40, however, the action of galnon is antagonized by M35 and M40 (FIG. 5).

The invention claimed is:
1. A method for quantifying G protein-coupled receptor (GPCR)-G protein binding by means of using a cell membrane array, said cell membrane array comprising (i) a support and (ii) cell membrane microdeposits of cell membrane preparations, wherein said support is coated with orthophosphoric acid and wherein said microdeposits are fixed to a support, said method comprising:
(i) putting an unlabeled candidate compound in contact with said cell membrane array in the presence of labeled GTP or of a labeled, non-hydrolyzable analog thereof, in conditions allowing the interaction between said compound and said GPCR present in said cell membranes, and between said labeled GTP or analog thereof and said G protein also present in said cell membranes;
(ii) washing said membrane array to eliminate said labeled GTP or labeled, non-hydrolyzable analog thereof that is not bound to said G protein; and
(iii) quantifying the signal obtained due to the binding of said labeled GTP or labeled, non-hydrolyzable analog thereof to said G protein.
2. A method according to claim 1, in which said non-hydrolyzable GTP analog is GTPγS.
3. A method according to claim 2, in which said GTPγS is labeled radioactively or with a fluorophore.

4. A method according to claim 3, in which said GTPγS is [$^{35}$S]GTPγS, 2'(3')-O—(N-methyl-3'-anthraniloyl)-GTPγS or BODIPY-FL-GTPγS.

5. A method according to claim 1, in which each of the microdeposits of said array is formed by isolated cell membranes from cell lines overexpressing a certain G protein-coupled receptor subtype or any genetic variation thereof.

6. A method according to claim 1, in which each of the microdeposits of said array is characterized by being formed by isolated membranes from cell lines overexpressing a certain G protein subtype or any genetic variation thereof.

7. A method according to claim 6, in which said G protein subtype is any of the possible subtypes of the three families, $G_s$, $G_{i/o}$, $G_q$.

8. A method according to claim 1, in which said candidate compound is a chemical compound or a biological product.

9. A method according to claim 8, in which said candidate compound is a chemical compound or a biological product with affinity and selectivity for a GPCR subtype.

10. A method according to claim 1, in which each of the microdeposits is formed by isolated membranes from (i) different tissue of one and the same subject, or (ii) one and the same tissue from different individuals, of one and the same species, of different species or of genetically modified species.

11. A method according to claim 10, in which said tissue from one and the same subject comes from one and the same organ or from different organs.

12. A method according to claim 1, in which each of the microdeposits is formed by isolated membranes from cell lines or tissue obtained from individuals with different pathologies and/or pharmacological treatments.

13. A method for analyzing GPCR-G protein binding and quantifying the effect promoted by this binding on a second intracellular messenger by means of using a cell membrane array, said cell membrane array comprising (i) a support and (ii) cell membrane microdeposits of cell membrane preparations, wherein said support is coated with orthophosphoric acid and wherein said microdeposits are fixed to a support, said method comprising:
(i) putting an unlabeled candidate compound in contact with said cell membrane array in the presence of GTP or of a non-hydrolyzable analog thereof and a labeled second cellular messenger formation activity marker, wherein said labeled second cellular messenger formation activity marker is selected from the group consisting of labeled ATP or a non-hydrolyzable analog thereof and labeled phosphatidylinositol 4,5 diphosphate (PtdIns(4,5)P2), in conditions allowing the interaction between said compound and said GPCR present in said cell membranes, between said GTP or analog thereof and said G protein present in said cell membranes, between the active G protein and an effector molecule also present in said cell membranes, and between said effector molecule and said labeled second cellular messenger formation activity marker;
(ii) washing said membrane array to eliminate said labeled second cellular messenger formation activity marker that is not bound to said effector molecule; and
(iii) quantifying the signal obtained due to the binding of said labeled second cellular messenger formation activity marker to said effector molecule, where the intensity of the signal obtained is proportional to the effect promoted by the GPCR-G protein binding on said second intracellular messenger.

14. A method according to claim 13, in which said GTP or non-hydrolyzable analog thereof is labeled.

15. A method according to claim 13, in which said non-hydrolyzable GTP analog is GTPγS.

16. A method according to claim 13, in which each of the microdeposits of said array is formed by isolated cell membranes from cell lines overexpressing a certain G protein-coupled receptor subtype or any genetic variation thereof.

17. A method according to claim 13, in which each of the microdeposits of said array is characterized by being formed by isolated membranes from cell lines overexpressing a certain G protein subtype or any genetic variation thereof.

18. A method according to any of claim 17, in which said G protein subtype is any of the possible subtypes of the three families, $G_s$, $G_{i/o}$ o $G_q$.

19. A method according to claim 13, in which said candidate compound is a chemical compound or a biological product.

20. A method according to claim 19, in which said candidate compound is a chemical compound or a biological product with affinity and selectivity for a GPCR subtype.

21. A method according to claim 13, in which each of the microdeposits is formed by isolated membranes from (i) different tissue of one and the same subject, or (ii) one and the same tissue from different individuals, of one and the same species, of different species or of genetically modified species.

22. A method according to claim 21, in which said tissue from one and the same subject comes from one and the same organ or from different organs.

23. A method according to claim 13, in which each of the microdeposits is formed by isolated membranes from cell lines or tissue obtained from individuals with differences in at least one of their pathologies and pharmacological treatments.

\* \* \* \* \*